United States Patent [19]

Teufel et al.

[11] 4,001,431

[45] Jan. 4, 1977

[54] DERIVATIVES OF THE 1,2-DIARYLETHYLENE-AND PHARMACEUTICAL COMPOSITIONS THEREOF

[75] Inventors: Hermann Teufel, Kelkheim, Taunus; Wilhelm Bartmann, Neuenhain, Taunus; Ernold Granzer, Kelkheim, Taunus; Josef Musil, Konigstein, Taunus, all of Germany

[73] Assignee: Hoechst Aktiengesellschaft, Frankfurt am Main, Germany

[22] Filed: Mar. 7, 1975

[21] Appl. No.: 556,221

[30] Foreign Application Priority Data

Mar. 9, 1974 Germany ........................ 2411325
Feb. 22, 1975 Germany ........................ 2507685

[52] U.S. Cl. .......................... 424/327; 260/465 F; 260/465 G; 260/566 A; 260/566 B; 260/566 D; 260/566 R; 260/599; 260/600 R; 424/304

[51] Int. Cl.$^2$ ............... A61K 31/15; C07C 131/00
[58] Field of Search ............... 260/566 A; 424/327

[56] References Cited

OTHER PUBLICATIONS

Z. Arnold et al. Collection Czechoslov Chem. Commun., 26, 3059–3073 (1961).
Sumitoma et al. Chemical Abstracts, vol. 72, 101238a (1970).

*Primary Examiner*—Lewis Gotts
*Assistant Examiner*—Dolph H. Torrence
*Attorney, Agent, or Firm*—Curtis, Morris & Safford

[57] ABSTRACT

The invention relates to derivatives of 1,2-diarylethylene and to a process for their preparation. The compounds have valuable pharmaceutical properties and may be used as medicaments.

3 Claims, No Drawings

DERIVATIVES OF THE 1,2-DIARYLETHYLENE- AND PHARMACEUTICAL COMPOSITIONS THEREOF

The invention relates to derivatives of 1,2-diarylethylene of the formula

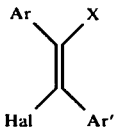

(I)

wherein X is a —CN or —CH=NOH group, Ar is phenyl substituted by one or two lower alkyl and/or lower alkoxy groups and/or halogen atoms or is unsubstituted phenyl if Ar' is substituted phenyl,
Ar' is phenyl substituted by one or two lower alkyl and/or lower alkoxy groups and/or halogen atoms or unsubstituted phenyl if Ar is substituted phenyl, and Hal is chlorine or bromine.

Lower alkyl or lower alkoxy means alkyl or alkoxy having 1 to 6 carbon atoms in a straight or branched chain.

The compounds have valuable pharmacological properties and may, therefore, be used as a medicament.

Compounds of the formula I a

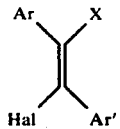

(Ia)

wherein X and Hal have the above meaning and Ar and Ar' are unsubstituted phenyl, have already been described, for example by Issei Iwai et al. in Chem. Pharm. Bull, 12, 1446 (1964) and Z. Arnold et al. in Cal. Czechoslov. Chem. Comm. 26. 3059 (1961). However, a pharmacological activity for these compounds has not been mentioned.

Thus, besides compounds of the formula I and a process for their preparation, the invention relates to pharmaceutical compositions consisting of or containing a compound of the formula I or a compound of the formula Ia, as well as to the use of compounds of the formulas I and Ia as medicaments or in medicaments.

The process for preparing the compounds of the formula I comprises
a. converting 2,3-diaryl-3-halogen-acrylaldehydes of the general formula II

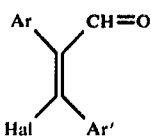

(II)

into aldimine derivatives of the formula III

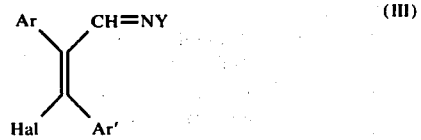

(III)

wherein Ar, Ar' and Hal have the meaning indicated for the compounds of the formula I, and Y is a hydroxy group, a functional derivative of a hydroxy group suitable for being split off, a halogen atom, a hydrogen atom, or a dialkylamino group, and converting these, if desired, into compounds of the formula I, wherein X is a —CN group;

b. reacting corresponding 1,2-diaryl-acetylenes with halogen cyans to obtain compounds of the formula I, wherein X is a —CN group.

The conversion of aldehydes of the formula II into compounds of the formula I, wherein X is a —CH=NOH group is effected according to methods known for the preparation of oximes with hydroxyl amine. The reaction is preferably carried out in the presence of solvents. Organic solvents miscible with water such as alcohols, dioxan, etc., or tertiary organic bases such as pyridine are suitable.

The following aldimine intermediate stages of the general formula III are considered, for example for the conversion into compounds of the formula I, wherein X is a —CN group.

OXIMES AND THEIR DERIVATIVES

Oximes may be converted into the corresponding nitriles by direct dehydration, for example with mineral acids, with sodium formiate in formic acid or with sodium acetate in glacial acetic acid. In the case of sensitive oximes it is suitable to convert the hydroxyl group of the oxime before elimination into a better leaving group. The following methods may be used for example: reaction with alkyl- or arylsulfonic acid chlorides or with thionyl chloride, with carboxylic acid chlorides or anhydrides, with N,N'-dialkylcarbodiimides, etc. In many cases the isolation of the oxime derivatives III thus obtained is not necessary; the elimination often occurs spontaneously. Oxim-O-alkyl- or arylsulfonates obtained in this way may be converted into the corresponding nitriles under very mild conditions, for example with aluminum oxide in organic solvents such as chloroform or methylene chloride.

N-Chloraldimines, which are obtained from the aldehydes II with an aqueous chloro-amine solution and yield the nitriles I after the separation of hydrochloric acid.

Aldimines, which may be obtained by reacting the aldehydes with ammonia and may be converted into the nitriles I by oxidation for example with $O_2/CuCl_2$, $Pb(OAc)_4$ or corresponding compounds.

N,N-Dialkyl-hydrazones, which are obtained from the aldehydes with N,N-dialkyl-hydrazines and may be converted into the nitriles of the general formula I either by oxidation (for example with hydrogen peroxide) or by alkylic splitting of the corresponding methyl iodides.

The reaction according to the process (b) is preferably carried out with chlorocyan or bromocyan in a tetrachloro-ethane in the presence of the corresponding aluminum halides, preferably at elevated temperatures (cf. Issei Iwai et al., Chem. Pharm. Bull. 12, 1446 ff (1964)).

The 2,3-Diaryl-3-halogenacrylaldehydes II required as starting material may be prepared in a simple and known way from the corresponding desoxybenzoins [cf. M. Weissenfels, H. Schurig, G. Huhsam, Z. Chem. 6 471 (1966), cf. German Offenlegungsschrift No. 2 160 236].

1,2-Diaryl-acetylenes may be prepared, for example, from copper phenyl-acetylides and aryl-iodides according to the process described by R. D. Stephens et al. in J. Org. Chem. 28, 3313 (1963).

Especially preferred are compounds of the formula I, the aryl groups of which are phenyl radicals substituted by alkoxy, bromine or chlorine.

The compounds of the formulae I and Ia have valuable pharmacological properties. Especially they have a strong hypouricemic, and uricosuric and hypolipidemic action.

In the mentioned test situations the hypouricemic and uricosuric action on male Wistar rats appeared independently from further pharmacological actions, such as the oestrogenic action, action on the sodium-potassium retention or excretion, and action on the lipid metabolism. For this reason it is possible to use the substances mentioned, after the usual toxicological and clinical tests, as a therapeutical composition for different disorders of the purine metabolism, especially primary and secondary gout. The possible indications for which the substances may be used are listed in Table 1.

Substances having the properties mentioned not only have an influence on the lowering of the serum uric described in Table 1 and on the stabilization of the disturbed excretion of uric acid in the urine, but they may also be used for the normalization of disturbed metabolisms, mainly disorders of carbohydrate and lipid metabolism. Since in the case of the substances mentioned above a hypouricemic and uricosuric action have been proved, the substances may be suitable, in analogy to other known pharmaceutical compositions, as possible therapeutical compositions to influence disorders of the nucleic acid metabolism and to increase antimetabolic action (6-mercaptopurine).

The frequency of the diseases mentioned is 2 % of the male population and 0.2 to 0.7 % in the female population of the civilized countries; the frequency of the diseases is increasing. Therapy of hyperuricemiae must be considered not only as necessary for the essential pathophysiological disturbance, but also as an influence on the risk of arteriosclerosis.

The uricosuric and hypouricemic activity have been observed by way of experiment on the oxonate rat (in each case on 8 test animals). In this test arrangement the uricase activity of the rat liver is inhibited by the administration of potassium oxonate and, thus, a disorder of the purine metabolism similar to gout is initiated. The activity has been tested in two test arrangements.

1. The influence of the disorder of purine metabolism similar to gout which has been initiated by way of experiment has been tested in a 3-day-cycle. 18 hours before the first test day, a 0.5 % potassium oxonate solution was administered to the rats ad libitum. On the first and the second test day the substances to be tested were administered to the animals per esophagal sound. The urine samples were examined on the first, second and third day, and the blood sample was examined on the third test day to determine the content of uric acid. Additionally the concentration of creatinine, of sodium, potassium and chloride was determined in the urine and serum samples. The results are listed in Table 2.

2. The influence of the similar disorder of the purine metabolism initiated by way of experiment was examined in a 24-hours' test. In this test arrangement, after withdrawal of water and food for 18 hours for the animals, the substances are introduced by means of an esophagal sound into the stomach. After 8 hours, 5 ml/100 g/kg of water are additionally introduced into the stomach per esophagal sound. After 24 hours the urine samples are taken, the animals are killed in the ether narcosis and blood and urine are analyzed according to the same parameters, as in 1. The results of this test are listed in Table 3.

TABLE 1

Hyperuricemia: causes
1. Increased de-novo-synthesis of uric acid:
   a. Gout caused by hyperproduction
   b. Lesh-Nyhan syndrome
   c. Lymphoproliferative diseases
   d. Zytostatic therapy
   e. Glycogenosis (type I)
   f. Sickle cell anemia
2. Pyelopathy:
   a. Lowering of the filtration rate, lowering of the tubular secretion or combination of both
      i. Renal insufficiency
      ii. Renal gout
      iii. Lead nephropathy
   b. Competitive secondary lowering of excretion of uric acid
      i. Organic acids, thiazides, para-amino-hippuric acid
         low dosage units of the uricosuric agents
      ii. Increase of lactate (lactacidosis or after alcohol intake)
      iii. (diabetic) Ketoacidosis
      iv. Glycogenosis (type II)
3. Consequences of other disturbances of the metabolism:
   a. Diabetes
   b. Coronary diseases
   c. Hypertonia

TABLE 2

| | Test for uricosuric action Compound of Example 13 | | | | |
|---|---|---|---|---|---|
| | 1st | | 2nd | | 3rd day |
| | excretion of uric acid urine mg/24 hours | | | | |
| | x ± SD***) | % | x ± SD | % | x ± SD | % |
| Control | | | | | | |
| group oxonate | 5.99 ± 2.5 | 100 | 4.73 ± 4.1 | 100 | 2.55 ± 1.0 | 100 |
| 0.3 mg/Kg | 7.12 ± 6.0 | 118 | *12.04 ± 7.1 | 254 | *9.50 ± 6.6 | 372 |
| 3.0 mg/Kg | 8.88 ± 4.8 | 148 | 9.53 ± 4.9 | 201 | 7.69 ± 7.4 | 301 |
| Probeneckle*) | | | | | | |

TABLE 2-continued

| 50 mg/kg | 6.31 ± 2.6 | 105 | 10.8 ± 6.6 | 229 | 8.9 ± 3.6 | 349 |

° = statistically significant p<0.05 (Duncan-test)
*⁾ = p-(N,N-di-n-propyl-sulfamoyl)-benzoic acid
**⁾ = 1H-Pyrazolo/3.4.d/-pyrimidin-4-ol
***⁾ = standard deviation

TABLE 3

Test for uricosuric and hypouricemic action
Compound of Example 10

|  | Excretion of uric acid mg/24 hours | | 24 hours test Serum-uric acid mg/% | |
|---|---|---|---|---|
|  | x ± SD | % | x ± SD | % |
| Control group oxonate | 5.86 ± 1.5 | 100 | 2.06 ± 0.28 | 100 |
| 0.3 mg/Kg | °9.13 ± 2.1 | 155 | 2.01 ± 1.0 | 97 |
| 3.0 mg/Kg | °10.48 ± 3.1 | 178 | 1.68 ± 0.43 | 81 |

Compound of Example 6

| Control group oxonate | 6.37 ± 2.2 | 100 | 4.37 ± 0.9 | 100 |
|---|---|---|---|---|
| 0.3 mg/Kg | 5.56 ± 2.0 | 87 | 3.05 ± 0.2 | 69 |
| 3.0 ,g/Kg | 6.05 ± 3.6 | 94 | °2.9 ± 0.6 | 66 |
| Allopurinol**⁾ 50 mg/Kg | 6,74 ± 3.0 | 105 | 3.77 ± 0.3 | 86 |

° = statistically significant p<0.05 (Duncan-test)
*⁾ = p-(N,N-di-n-propyl-sulfamoyl)-benzoic acid
**⁾ = 1H-Pyrazolo/3.4.d/-pyrimidin-4-ol
***⁾ = standard deviation The compounds of the formulae I and Ia have, furthermore, a strong hypolipidemic action; therefore, they may be used for the therapy of primary hyperlipidemiae and certain secondary hyperlipidemiae, such as for example in the case of diabetes. Since hyperlipemia is the most dangerous cause of coronary heart diseases and, generally speaking, elevated serum lipid values involve a great risk of causing arteriosclerotic diseases also of different localization and not only of the coronary vessels, the reduction of elevated serum lipid levels is extremely important for the prevention and therapy of arteriosclerosis, especially, of the coronary heart vessels. Being able to reduce normal and elevated serum lipid levels in animals, the above-specified substances are useful for the treatment and prevention of arteriosclerotic diseases, especially of the coronary vessels but also of other blood vessels.

The hypdipidemic activity of the compounds mentioned could, inter alia, be demonstrated by the following tests:

1. Male rats having a normal serum lipid content. The values indicated in Table 4 stand for a change in the serum concentrations of certain lipid classes after an eight days' treatment in different daily dosage forms mentioned. The doses were administered per os by means of an esophagal sound. Generally, prior to and after the treatment, blood samples were taken and the concentration of cholesterol in the serum was determined according to the method of Lauber and Richterich and that of triglycerides according to the method of Eggstein and Kreutz. In the Examples of the following Table 4, the changes in the serum lipid values due to the treatment with the substances are defined as follows:

a. The changes in percent of the final value of the treated group, referred to the initial value of the treated group, the initial value being 100 percent and b. the change in the final value of the treated group, referred to the final value of an accompanying untreated control group (Placebo group), the untreated control group's value being defined als 100 percent. Thus, the value given before a cross-line is the change in percentage referred to the initial value, the value given after a cross-line is the change in percentage of the treated group, referred to the untreated control group.

2. The hypertriglyceridemia induced by carbohydrates and initiated by fructose doses in male rats was substantially reduced by a three-day oral pre-treatment with the cited substances in comparison to an untreated control group (Table 5).

TABLE 4

| Compound of Example | serum cholesterol | 10 mg/kg serum-triglycerides | serum-cholesterol | 0.1 mg/kg serum-triglycerides |
|---|---|---|---|---|
| 13 | −61/−45 | −82/−74 | −38/−17 | −10/ |
| 14 | −14/−5 | − 3/− 4 |  |  |
| 15 | −15/−6 | −15/−22 |  |  |
| Clofibrate | −25/−17 | −21/−15 | (dosage 100 mg/kg) | |

Change in percent on the male rat with mg/kg/day after eight oral applications.

TABLE 5

| Compound of Example | Serum cholesterol | 3 mg/kg Serum triglycerides |
|---|---|---|
| 13 | −37 | −47 |
| Clofibrate (ten times the dose) |  | −20 |

Change in percent of the hypertriglyceridemiae induced by carbohydrates of the male rats after a three-day pre-treatment per os with the doses indicated.

The novel compounds may be administered either as such or in admixture with pharmacologically acceptable carriers, an oral dosage unit from being preferred. For this purpose the active compounds may be mixed with known excipients and brought into suitable dosage unit forms according to known methods, for example into granules, tablets, hard gelatine capsules, aqueous or oily suspensions or aqueous or oily solutions. As inert carriers and auxiliaries, there may for example be mentioned diluents, such as magnesium carbonate, lactose or corn starch with the addition of other substances, as for example magnesium stearate. The compositions may be obtained by dry or moist granulation.

As oily carriers or solvents there are considered especially vegetal or animal oils, for example sunflower oil or codliver oil. As individual dose there are considered about $10^{-2}$ to 10 mg/kg, preferably 0.2 to 1 mg/kg. A dosage unit contains for example 0.5 to 200 mg, preferably 1 to 100 mg of active substance of the formula I or Ia.

A special use of the compounds is in combination with other active substances. In addition to other suitable substances the following ones may be mentioned: Antidiabetics, such, for example, as glycodazine, tolbutamide, glibenclamine, phenformine, buformine, metformine or agents acting on the circulatory system in a larger sense, but especially those dilating the coronary vessels, such, for example, as chromonar or prenyl amine and blood pressure lowering substances, such, for example, as Reserpin, α-methyl-dopa or clonidines, further agents lowering the lipid level, or geriatrics, psychopharmaceutics such as chlorodiazepoxides, diazepam, and meprobamate, or vitamins.

The following Examples illustrate the invention.

EXAMPLE 1

1. 2,3-bis(4-methoxyphenyl)-3-chloro-acrylaldoxime 30.2 g of 2,3-bis(4-methoxyphenyl)-3-chloro-acrylaldehyde (0.1 mol) were dissolved in 250 ml of pyridine and heated for half an hour on the steam bath together with 30 g of hydroxylamine hydrochloride. Then the solution was evaporated; the remaining solid substance was taken up with ethanol. The whole was boiled, suction-filtered and dried.

The 2,3-bis(4-methoxyphenyl)-3-chloro-acrylaldoxime had a melting point of from 207° to 208° C (decompositon).

The following compounds were prepared according to the same process:

2. 2-Phenyl-3-(4-bromophenyl)-3-chloro-acrylaldoxime
   M.P.: 217° to 218° C (decomp.).
3. 2-Phenyl-3-p-tolyl-3-chloro-acrylaldoxime
   M.P.: 212° to 213° C (decomp.).
4. 2-Phenyl-3-(4-methoxyphenyl)-3-chloro-acrylaldoxime
   M.P.: 211° to 212° C (decomp.).
5. 2-(p-Methoxyphenyl)-3-p-tolyl-3-chloro-acrylaldoxime
   M.P.: 222° to 223° C (decomp.).
6. 2-(p-Methoxyphenyl)-3-phenyl-3-chloro-acrylaldoxime
   M.P.: 216° to 217° C (decomp.).
7. 2-Phenyl-3-(p-ethoxyphenyl)-3-chloro-acrylaldoxime
   M.P. 219° to 220° C (decomp.).
8. 2-Phenyl-3-(p-n-butoxyphenyl)-3-chloro-acrylaldoxime
   M.P.: 158° to 159° C (decomp.).
9. 2,3-Diphenyl-3-chloro-acrylaldoxime
   M.P.: 210° to 211° C (decomp.).
10. 2.3-Diphenyl-3-bromo-acrylaldoxime
    M.P.: 205° to 206° C (decomp.).
11. 2,3-Bis(4-methoxyphenyl)-3-bromo-acrylaldoxime
    M.P.: 176° to 178° C (decomp.).
12. 2-Phenyl-3-(3,4-dimethoxyphenyl)-3-chloro-acrylaldoxime
    M.P.: 174° to 175° C (decomp.).
13. 2,3-Bis(4-methoxyphenyl)-3-chloro-acrylonitrile 1.0 g of 2,3-Bis(4-methoxyphenyl)-3-chloro-acrylaldoxime (3.14 m moles) was refluxed for 2 hours in 25 ml of acetanhydride. After cooling, the mixture was poured onto water. The crystalline solid substance which had precipitated was suction-filtered and recrystallized from methanol. Melting point: 140° to 142° C.

14. 2-Phenyl-3-(4-bromophenyl)3-chloro-acrylonitrile 2g of 2-phenyl-3-(4-bromophenyl)-3-chloro-acrylaldoxime (5.9 m moles) were suspended in 50 ml of THF. The mixture was cooled to 0° C and, successively, 5 ml of sodium hydroxide solution and 1.14 g of p-toluene-sulfochloride were added. The mixture was stirred for 1 hour at 10° C and evaporated at room temperature. The solid residue was taken up with a small amount of methylene chloride and applied onto a column with basic aluminum oxide in n-hexane. Elution was effected with petroleum ether and then with methylene chloride. In this way pure 2-phenyl-3-(4-bromophenyl)-3-chloro-acrylonitrile (melting point: 128°-130° C) was obtained.

The same compound was obtained:

1. by reaction of the oxime with sodium acetate-glacial acetic acid at 110° C, reaction time: three hours. After cooling, the whole was poured onto water and recrystallized;
2. by reaction of the oxime with concentrated H₂SO₄ at 100° C for 5 minutes. Working up: pouring into ice water, recrystallization of the solid substance precipitated.

The following compounds were obtained as described under 14a:

15. 2-Phenyl-3-p-tolyl-3-chloro-acrylonitrile
    M.P.: 108° to 109° C.
16. 2-Phenyl-3-(4-methoxyphenyl)-3-chloro-acrylonitrile acrylonitrile
    M.P.: 99° to 100° C.
17. 2,3-Bis-phenyl-3-chloro-acrylonitrile
    M.P.: 78° to 81° C.
18. 2-p-Methoxyphenyl-3-p-tolyl-3-chloro-acrylonitrile
    M.P.: 127° to 129° C.
19. 2-p-Methoxyphenyl-3-phenyl-3-chloro-acrylonitrile
    M.P.: 111° to 112° C.
20. 2-Phenyl-3-p-ethoxyphenyl-3-chloro-acrylonitrile
    M.P.: 106° to 107° C.
21. 2,3-Bis(p-methoxyphenyl)-3-brom-acrylonitrile
    M.P.: 100° to 101° C.
22. 2,3-Bis-phenyl-3-bromo-acrylonitrile
    M.P.: 95° to 96° C.
23. 50 mg of 2,3-diphenyl-3-bromo-acrylaldoxime were mixed together with 25 to 30 % by weight of lactose as carrier, 10 to 15 % by weight of starch as disintegrating agent and 1 to 5 % by weight of polyvinyl pyrrolidone as granulating agent and compressed to a tablet.

What we claim is:

1. A 1,2-diaryl-ethylene of the formula

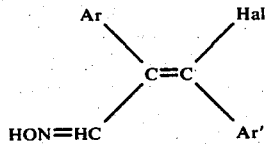

wherein Hal is chlorine or bromine and Ar and Ar' are each phenyl substituted by one or two members selected from the group consisting of lower alkyl, lower alkoxy, and halogen, or one of Ar and Ar' is phenyl and the other is substituted phenyl.

2. A pharmaceutical composition comprising, in combination with a pharmaceutical carrier, an effective ingredient which is a compound of the formula

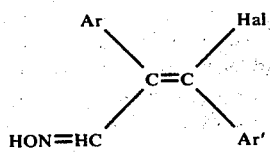

wherein Hal is chlorine or bromine and Ar and Ar', which are the same or different, are phenyl or phenyl substituted by one or two members selected from the group consisting of lower alkyl, lower alkoxy, and halogen.

3. A method for treating disorders of purine metabolism, hyperlipidemiae, or both conditions, in a patient suffering therefrom, which method comprises administering an effective amount of at least one compound selected from the group consisting of compounds of the formula

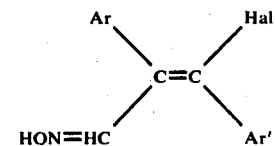

wherein Hal is chlorine or bromine and Ar and Ar', which are the same or different, are phenyl or phenyl substituted by one or two members selected from the group consisting of lower alkyl, lower alkoxy, and halogen.

* * * * *